US00PP25353P2

(12) United States Plant Patent
Pieters

(10) Patent No.: US PP25,353 P2
(45) Date of Patent: Mar. 17, 2015

(54) ***CHRYSANTHEMUM* PLANT NAMED 'SALOMON SURFER'**

(50) Latin Name: *Chrysanthemum×morifolium*
Varietal Denomination: Salomon Surfer

(71) Applicant: Luc Remi Johan Pieters, Staden-Oostnieuwkerke (BE)

(72) Inventor: Luc Remi Johan Pieters, Staden-Oostnieuwkerke (BE)

(73) Assignee: Pieters Joseph & Luc B.V.B.A., Staden-Oostnieuwkerke (BE)

( * ) Notice: Subject to any disclaimer, the term of this patent is extended or adjusted under 35 U.S.C. 154(b) by 129 days.

(21) Appl. No.: 13/815,608

(22) Filed: Mar. 11, 2013

(51) Int. Cl.
*A01H 5/00* (2006.01)

(52) U.S. Cl.
USPC ..... Plt./287

(58) Field of Classification Search
CPC ..... A01H 5/00
USPC ..... Plt./287
See application file for complete search history.

*Primary Examiner* — Susan McCormick Ewoldt
(74) *Attorney, Agent, or Firm* — C. A. Whealy

(57) ABSTRACT

A new and distinct cultivar of *Chrysanthemum* plant named 'Salomon Surfer', characterized by its uniform, upright, broadly spreading and mounding plant habit; moderately vigorous to vigorous growth habit; freely branching habit; dense and full plant habit; early, uniform and freely flowering habit; large decorative-type inflorescences with light purple-colored ray florets; and good garden performance.

2 Drawing Sheets

Botanical designation: *Chrysanthemum×morifolium*.
Cultivar denomination: 'SALOMON SURFER'.

BACKGROUND OF THE INVENTION

The present invention relates to a new and distinct cultivar of *Chrysanthemum* plant, botanically known as *Chrysanthemum×morifolium* and hereinafter referred to by the name 'Salomon Surfer'.

The new *Chrysanthemum* plant is a product of a planned breeding program conducted by the Inventor in Staden-Oostnieuwkerke, Belgium. The objective of the breeding program is to create new uniform and freely-flowering hardy *Chrysanthemum* plants with attractive inflorescence form and floret coloration.

The new *Chrysanthemum* plant originated from a cross-pollination made by the Inventor in Staden-Oostnieuwkerke, Belgium in October, 2008, of a proprietary selection of *Chrysanthemum×morifolium* identified as code number 6008, not patented, as the female, or seed parent with *Chrysanthemum×morifolium* 'Maribelle Mauve', not patented, as the male, or pollen, parent. The new *Chrysanthemum* plant was discovered and selected by the Inventor as a flowering plant from within the progeny of the stated cross-pollination in a controlled greenhouse environment in Staden-Oostnieuwkerke, Belgium in October, 2009.

Asexual reproduction of the new *Chrysanthemum* plant by vegetative cuttings was first conducted in a controlled greenhouse environment in Staden-Oostnieuwkerke, Belgium in January, 2010. Asexual reproduction by cuttings has shown that the unique features of this new *Chrysanthemum* plant are stable and reproduced true to type in successive generations.

SUMMARY OF THE INVENTION

Plants of the new *Chrysanthemum* have not been observed under all possible environmental conditions and cultural conditions. The phenotype may vary somewhat with variations in environmental conditions such as temperature, daylength and light intensity, without, however, any variance in genotype.

The following traits have been repeatedly observed and are determined to be the unique characteristics of 'Salomon Surfer'. These characteristics in combination distinguish 'Salomon Surfer' as a new and distinct *Chrysanthemum* plant:

1. Uniform, upright, broadly spreading and mounding plant habit; moderately vigorous to vigorous growth habit.
2. Freely branching habit; dense and full plant habit.
3. Early, uniform and freely flowering habit.
4. Large decorative-type inflorescences with light purple-colored ray florets.
5. Good garden performance.

Plants of the new *Chrysanthemum* differ primarily from the female parent selection in the following characteristics:

1. Plants of the new *Chrysanthemum* have larger inflorescences than plants of the female parent selection.
2. Under natural season conditions in Belgium, plants of the new *Chrysanthemum* flower about five days later than plants of the female parent selection.
3. Plants of the new *Chrysanthemum* and the female parent selection differ in ray floret color as plants of the female parent selection have pink-colored ray florets.

Plants of the new *Chrysanthemum* differ primarily from the male parent, 'Maribelle Mauve', in the following characteristics:

1. Plants of the new *Chrysanthemum* have larger inflorescences than plants of 'Maribelle Mauve'.
2. Under natural season conditions in Belgium, plants of the new *Chrysanthemum* flower about September $10^{th}$ whereas plants of 'Maribelle Mauve' flower about October $25^{th}$.

Plants of the new *Chrysanthemum* can be compared to plants of *Chrysanthemum×morifolium* 'Sea Surfer', not patented. In side-by-side comparisons conducted under natural season conditions in Staden-Oostnieuwkerke, Belgium, plants of the new *Chrysanthemum* differed from plants of 'Sea Surfer' in the following characteristics:

1. Plants of the new *Chrysanthemum* were more mounding than and not as upright as plants of 'Sea Surfer'.
2. Plants of the new *Chrysanthemum* had larger inflorescences than plants of 'Sea Surfer'.
3. Plants of the new *Chrysanthemum* and 'Sea Surfer' differed in ray floret color as plants of 'Sea Surfer' had pink-colored ray florets.

BRIEF DESCRIPTION OF THE PHOTOGRAPHS

The accompanying photographs illustrate the overall appearance of the new *Chrysanthemum* plant showing the colors as true as it is reasonably possible to obtain in colored reproductions of this type. Colors in the photographs may differ slightly from the color values cited in the detailed botanical description which accurately describe the colors of the new *Chrysanthemum* plant.

The photograph on the first sheet comprises a side perspective view of a typical flowering plant of 'Salomon Surfer' grown in a container.

The photograph on the second sheet are close-up views of the upper and lower surfaces of typical inflorescences (left) and upper and lower surfaces of typical leaves (right) of 'Salomon Surfer'.

DETAILED BOTANICAL DESCRIPTION

The aforementioned photographs and following observations and measurements describe plants grown during the summer and autumn in 17-cm containers in an outdoor nursery in Staden-Oostnieuwkerke, Belgium and under conditions and cultural practices typical of commercial *Chrysanthemum* production. During the production of the plants, day temperatures ranged from 10° C. to 25° C. and night temperatures ranged from 5° C. to 15° C. Plants were 5.5 months old when the photographs and description were taken. In the following description, color references are made to The Royal Horticultural Society Colour Chart, 2007 Edition, except where general terms of ordinary dictionary significance are used.

Botanical classification: *Chrysanthemum×morifolium* 'Salomon Surfer'.

Parentage:

*Female, or seed, parent*.—Proprietary selection of *Chrysanthemum×morifolium* identified as code number 6008, not patented.

*Male or pollen parent*.—*Chrysanthemum×morifolium* 'Maribelle Mauve', not patented.

Propagation:

*Type*.—Terminal vegetative cuttings.

*Time to initiate roots, summer*.—About 14 days at temperatures about 20° C.

*Time to initiate roots, winter*.—About 20 days at temperatures about 20° C.

*Time to produce a rooted young plant, summer*.—About 30 days at temperatures about 20° C.

*Time to produce a rooted young plant, winter*.—About 40 days at temperatures about 20° C.

*Root description*.—Fine, fibrous; light brown in color.

*Rooting habit*.—Freely branching; medium density.

Plant description:

*Plant and growth habit*.—Perennial *Chrysanthemum* plant with decorative type inflorescences; stems upright and broadly spreading giving a uniformly mounding appearance to the plant; very freely branching habit with about 145 lateral branches developing per plant; pinching enhances lateral branch development; dense and full plant habit; moderately vigorous to vigorous growth habit.

*Plant height*.—About 38 cm.

*Plant width*.—About 67.3 cm.

*Lateral branches*.—Length: About 13.7 cm. Diameter: About 3 mm. Internode length: About 1.9 cm. Strength: Strong. Aspect: Lateral branches positioned about 60° from the main stem. Texture: Densely pubescent; longitudinally ridged. Color: Close to 146D.

*Leaves*.—Arrangement: Alternate, simple. Length: About 3.8 cm. Width: About 2.6 cm. Shape: Broadly ovate; three to five-lobed Apex: Abruptly acute. Base: Attenuate. Margin: Palmately lobed and coarsely serrate, sinuses slightly convergent to parallel. Texture, upper surface: Moderately pubescent. Texture, lower surface: Densely pubescent. Venation pattern: Pinnate. Color: Developing leaves, upper surface: Close to 137A. Developing leaves, lower surface: Between 138A and 147B. Fully expanded leaves, upper surface: Close to 137B; venation, close to 143C. Fully expanded leaves, lower surface: Between 138A and 147B; venation, close to 144A to 144B. Petioles: Length: About 9 mm. Diameter: About 1 mm by 2 mm. Texture, upper and lower surfaces: Densely pubescent. Color, upper surface: Close to 144A. Color, lower surface: Close to 144A to 144B.

Inflorescence description:

*Form and arrangement*.—Decorative inflorescence form; relatively large inflorescences borne on terminals above foliar plane; disc and ray florets arranged acropetally on a capitulum.

*Fragrance*.—Faintly fragrant, pungent.

*Flowering response*.—Under natural season conditions, plants begin flowering about September 10$^{th}$ in Belgium.

*Postproduction longevity*.—Inflorescences maintain good color and substance for about three weeks in an outdoor nursery; inflorescences not persistent.

*Quantity of inflorescences*.—About four inflorescences develop per lateral branch; about 2,500 inflorescences develop per plant.

*Inflorescence buds*.—Height: About 5 mm. Diameter: About 7 mm. Shape: Flattened globular. Color: Close to 137C.

*Inflorescence diameter*.—About 4.5 cm.

*Inflorescence depth (height)*.—About 1.7 cm.

*Disc diameter*.—About 5 mm.

*Receptacle diameter*.—About 4 mm.

*Receptacle height*.—About 5 mm.

*Receptacle color*.—Close to 145C to 145D.

*Ray florets*.—Number of ray florets per inflorescence: About 210 arranged in about nine whorls. Length: About 1.7 cm. Width: About 5 mm. Shape: Narrowly ovate to narrowly oblong. Apex: Obtuse. Base: Cuneate. Margin: Entire. Aspect: About 50° from vertical. Texture, upper surface: Smooth, glabrous; slightly velvety; very slightly longitudinally ridged. Texture, lower surface: Smooth, glabrous; longitudinally ridged. Color: When opening, upper surface: Close to 70B. When opening, lower surface: Close to 75B to 75C. Fully opened, upper surface: Close to 75A; color does not change with development. Fully opened, lower surface: Close to 77C; color does not change with development.

*Disc florets*.—Number of disc florets per inflorescence: About five at the center of the inflorescence. Length: About 5 mm. Diameter: About 1.5 mm. Shape: Lower 80% fused into a tube; free apices are acute. Texture, inner and outer surfaces: Smooth, glabrous. Color: Towards the apex, close to 13A; mid-section and base, close to 145C to 145D.

*Phyllaries*.—Number of phyllaries per inflorescence: About 16 arranged in about two whorls. Length: About 7 mm. Width: About 2 mm. Shape: Oblong. Apex: Bluntly acute. Base: Cuneate. Margin: Entire. Texture, upper surface: Smooth, glabrous. Texture, lower surface: Pubescent. Color, upper surface: Close to 143A; margins, close to 195C. Color, lower surface: Close to 143B; margins, close to 195C.

*Peduncles*.—Length, terminal peduncle: About 8.9 cm. Length, fourth peduncle: About 8.9 cm. Diameter: About 1.5 mm. Aspect: Erect to about 35° from vertical. Strength: Strong. Texture: Densely pubescent. Color: Close to 138B to 138C.

*Reproductive organs*.—Androecium: Present only on disc florets. Number of stamens per floret: Five. Filament length: About 1 mm. Filament color: Close to 150D. Anther length: About 1.2 mm. Anther shape: Narrowly oblong. Anther color: Close to 154D. Pollen amount: Scarce. Pollen color: Close to 13A. Gynoecium: Present on ray and disc florets. Number of pistils per floret: One. Pistil length: About 4 mm. Style length: About 3.5 mm. Style color: Close to 150D. Stigma shape: Cleft, decurrent. Stigma color: Close to 9A to 9B. Ovary color: Close to 144C.

*Seeds and fruits*.—Seed and fruit development have not been observed on plants of the new *Chrysanthemum*.

Disease & pest resistance: Plants of the new *Chrysanthemum* have not been observed to be resistant to pathogens and pests common to *Chrysanthemum* plants grown under commercial conditions.

Garden performance: Plants of the new *Chrysanthemum* have good garden performance, are hardy to USDA Hardiness Zones 7 to 8 and tolerate high temperatures of about 35° C.

It is claimed:

1. A new and distinct *Chrysanthemum* plant named 'Salomon Surfer' as illustrated and described.

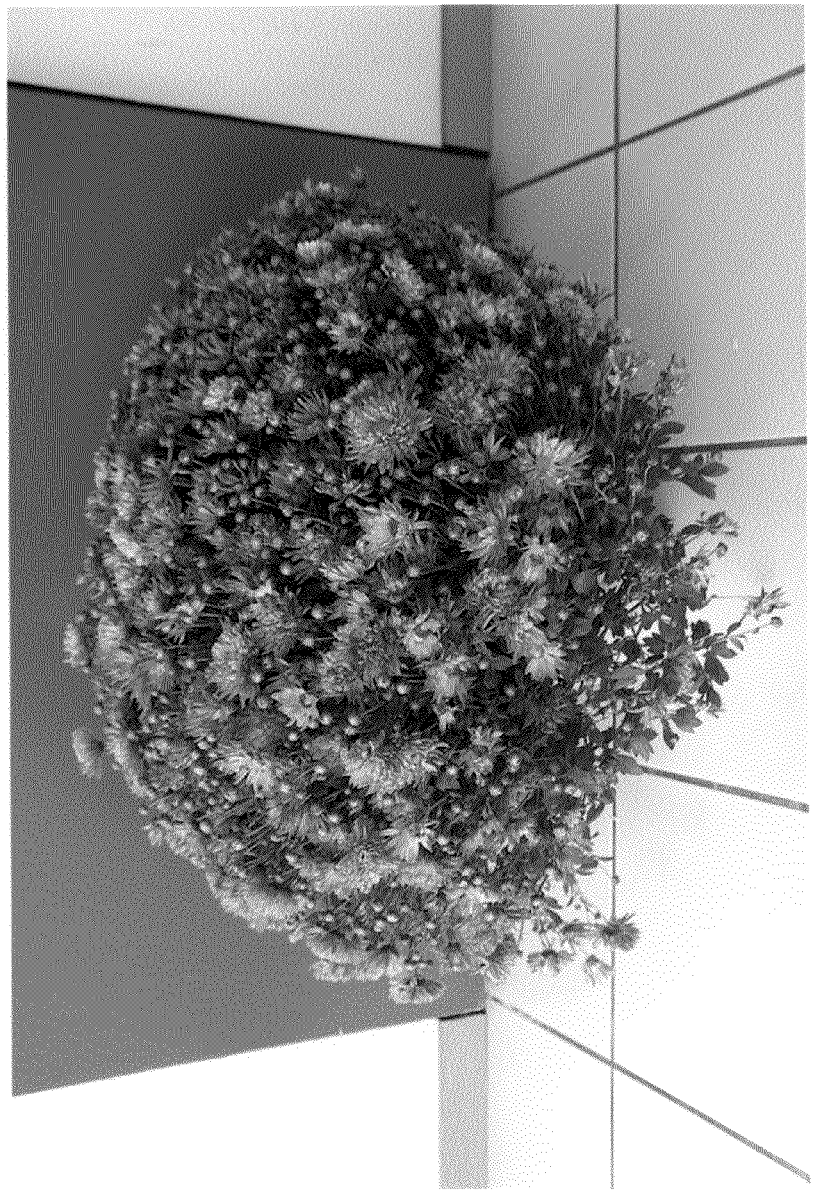

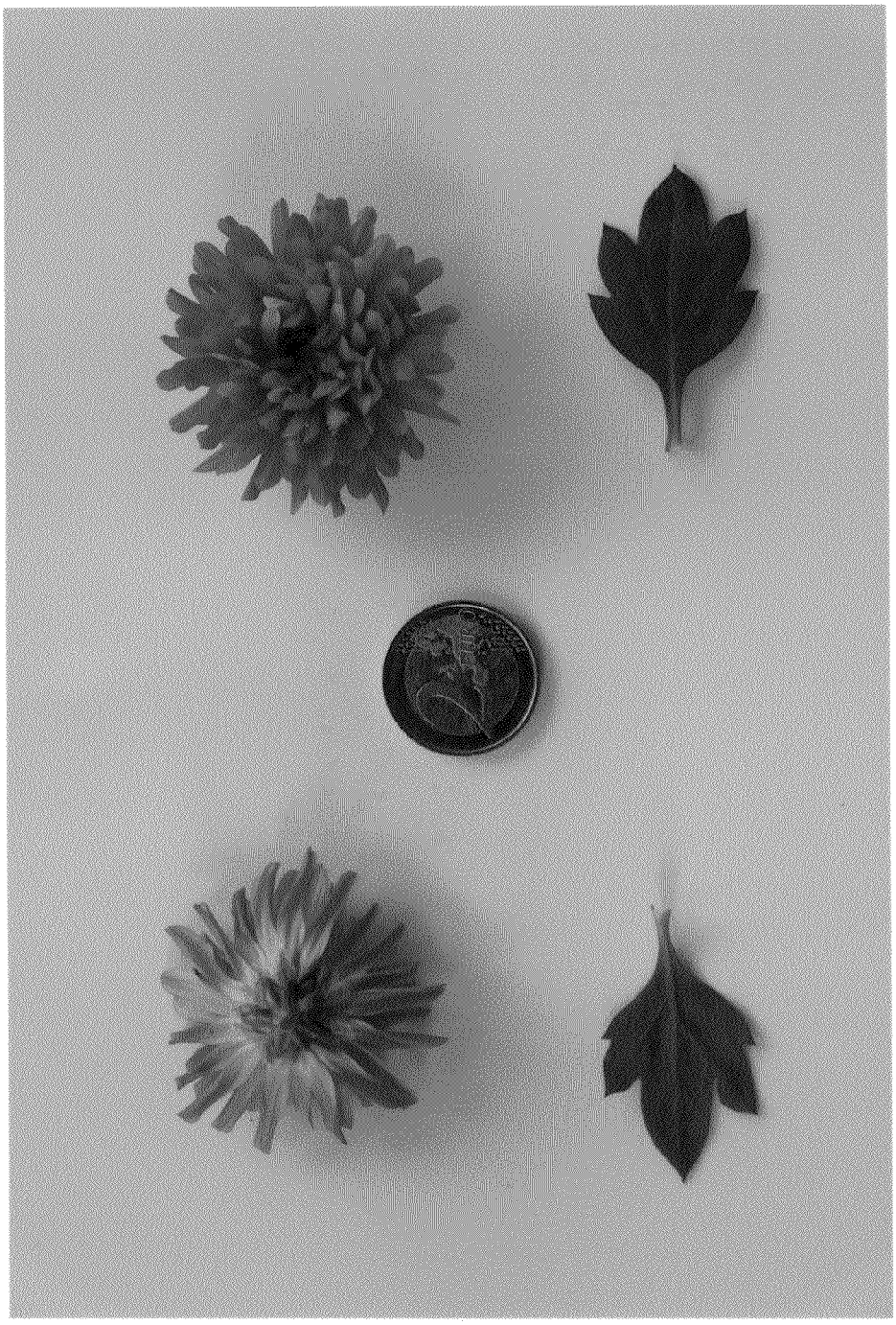

* * * * *